(12) United States Patent
Richards et al.

(10) Patent No.: US 6,468,504 B1
(45) Date of Patent: *Oct. 22, 2002

(54) COMPOSITION COMPRISING METHYLPHENIDATE AND ANOTHER DRUG

(75) Inventors: Andrew John McGlashan Richards; Nicholas Robert Pope, both of Cambridge (GB)

(73) Assignee: Medeva Europe, Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/597,384

(22) Filed: Jun. 19, 2000

Related U.S. Application Data

(63) Continuation of application No. 09/106,870, filed on Jun. 29, 1998, now Pat. No. 6,113,879, which is a continuation of application No. 08/679,878, filed on Jul. 15, 1996, now Pat. No. 5,773,478.

(30) Foreign Application Priority Data

| Jul. 14, 1995 | (GB) | 9514450 |
| Apr. 23, 1996 | (GB) | 9608390 |

(51) Int. Cl.[7] .......... A61K 49/00; A61K 9/16; A01N 33/02; A01N 43/06

(52) U.S. Cl. .......... 424/9.1; 424/9.2; 424/490; 435/4; 435/7.4; 435/7.71; 435/7.91; 514/649; 514/922; 514/438

(58) Field of Search .......... 424/9.1, 9.2, 490; 435/4, 7.4, 7.71, 7.91; 514/649, 922, 438

(56) References Cited

U.S. PATENT DOCUMENTS 5,733,756 A    3/1998    Zeitlin et al.

OTHER PUBLICATIONS

Patrick, K.S. et al. (1987) "Pharmacology of the Enantiomers of the threo–Methylphenidate" *The Journal of Pharmacology and Experimental Therapeutics* 241(1):152–158.

Eckerman, D.A. et al. (1991) "Enantioselective Behavioral Effects of threo–Methylphenidate in Rats" *Pharmacology Biochemistry& Behavior* 40(4):875–880.

Aoyama, T. et al. (1994) "Pharmacokinetics and Pharmacodynamics of (+)–threo–Methylphenidate Enantiomer in Patients with Hypersomnia" *Clinical Pharmacology& Therapeutics* 55(3):270–276.

Arëns, E.J. (1991) "Racemic Therapeutics–Ethical and Regulatory Aspects" *Eur. J. Clin. Pharmacol.* 41:89–93.

Arëns, E.J. (1990) "Stereoselectivity in Pharmacodynamics and Pharmacokinetics" *Schweiz. Med. Wochenschr.* 120(5):131–134.

Tyndale, R.F. et al. (1991) "Neuronal Cytochrome P450IID1 (Debrisoquine/Sparteine–Type): Potent Inhibition of Activity by (−)–Cocaine and Nucleotide Sequence Identity to Human Hepatic P450 Gene CYP2D6" *Molecular Pharmacology, An International Journal* 40(1):63–68.

Rapport, M.D. et al. (1993) "Methylphenidate and Desipramine in Hospitalized Children: I. Separate and Combined Effects on Cognitive Function" *J. Am. Acad. Child. Adolesc. Psychiatry* 32(2):333–342, **abstract only.

Licamele, W.L. et al. (1989) "The Concurrent Use of Lithium and Methylphenidate in a Child" *J. Am. Acad. Child Adolesc. Psychiatry* 28(5):785–787, **abstract only.

Grob, C.S. et al. (1986) "Suspected Adverse Methylphenidate–imipramine Interactions in Children" *J. Dev. Behav. Pediatr.* 7(4):265–267, **abstract only.

Drimmer, E.J. et al. (1983) "Desipramine and Methylphenidate Combination Treatment for Depression: Case Report" *Am. J. Psychiatry* 140(2):241–242, **abstract only.

*Primary Examiner*—Ali R. Salimi
(74) *Attorney, Agent, or Firm*—Saliwanchik, Lloyd & Saliwanchik

(57) ABSTRACT

A process of treating a subject that is undergoing methylphenidate therapy and concomitant therapy with another drug undergoes or interferes with $P_{450}$ metabolism, wherein the methylphenidate is d-threo-methylphenidate.

14 Claims, No Drawings

COMPOSITION COMPRISING METHYLPHENIDATE AND ANOTHER DRUG

CROSS-REFERENCE TO RELATED APPLICATIONS

This application is a continuation of U.S. application Ser. No. 09/106,870, filed Jun. 29, 1998, now U.S. Pat. No. 6,113,879, which is a continuation of U.S. application Ser. No. 08/679,878, filed Jul. 15, 1996, now U.S. Pat. No. 5,773,478.

FIELD OF THE INVENTION

This invention relates to a new composition comprising methylphenidate and another drug, and also to new ways of using known drugs including d-threo-methylphenidate (abbreviated herein as dtmp).

BACKGROUND OF THE INVENTION

Methylphenidate is a known drug (although it is a controlled substance). It is used primarily to treat hyperactive children.

Methylphenidate is a chiral molecule. The properties of the enantiomers have been investigated to some extent, although the drug is still administered as the racemate. It is generally thought that dtmp is the active material, and that its antipode (ltmp) is metabolised more rapidly.

Methylphenidate is often administered in conjunction with other drugs. It is known that the concurrent administration of two drugs that act or are metabolised through the same metabolic pathway can block that pathway, leading to drug interaction.

Racemic methylphenidate is known to interact clinically with a variety of drugs, such as the tricyclic antidepressants (TCAs), necessitating reduction in the TCA dosage when co-administered to prevent drug interaction (Physicians Desk Reference, Guide to Drug Interactions, 1994).

It is generally believed that the separate enantiomers of chiral therapeutic drugs exhibit different toxicological profiles, with one usually being the main cause of the toxic effects of drug interactions; see Ariens, Schweiz. Med. Wochenschr. 120(5): 131–134 (1990). The basis for this is that each enantiomer will exhibit different preferences for the pathways of enzyme metabolism, e.g. the cytochrome $P_{450}$ pathways, and therefore co-administered drugs are blocked at different sites of metabolism.

SUMMARY OF THE INVENTION

It has been discovered that, surprisingly, both dtmp and ltmp similarly inhibit metabolism of other drugs by the cytochrome $P_{450}$ systems, in human microsomes. Further, the racemate is shown to have a greater inhibitory profile than either of the enantiomers, suggesting an interaction between the two. Administration of dtmp, substantially free of ltmp, will substantially reduce the inhibition of $P_{450}$ isozymes. This has beneficial effects for patients undergoing concurrent administration of other drugs. To avoid the resultant risk of drug-drug toxicity, the present invention involves the administration of that other drug and dtmp. The two drugs used in this invention may be administered sequentially, concurrently or simultaneously, by the same or separate means.

The discovery is based on data showing that, surprisingly, dtmp administration results in less toxicity in the mouse liver than racemic methylphenidate, possibly due to less inhibition of hepatic cytochrome $P_{450}$ enzymes. The experiments and data are summarised below. The invention is thus of particular utility in that proportion of the population in which the relevant enzymes have reduced efficiency, or that are receiving the cross-reacting drugs, e.g. SSRIs, in therapy of, say, anxiety or depression.

DESCRIPTION OF THE INVENTION

The dtmp that is used in this invention is substantially free of ltmp, e.g. in an enantiomeric excess (ee) of at least 70%, preferably at least 90%, and more preferably at least 95%. The dtmp may be substantially enantiopure. It may be used in the form of any suitable salt, e.g. the hydrochloride.

As indicated above, the dtmp and other drug may each be administered independently. The invention is not restricted to any particular route of administration, and it will be generally preferred that the respective drugs are administered by their preferred routes. Thus, the dtmp may be administered by the same means as racemic methylphenidate, e.g. in a sustained-release formulation, e.g. a coated tablet. More preferably, the formulation is as described in the copending Patent Application entitled "Sustained-Release Formulation of Methylphenidate", filed on the same date, also assigned to Chiroscience Limited, and claiming priority from British Patent Application No. 9514451.5. The relevant content of that Application is incorporated herein by reference. Advantages of the use of dtmp are also described therein, and may include linear kinetics within the clinically relevant dose range, the reduction of exposure to a controlled substance, reduced side-effects (which include anorexia, insomnia, stomach ache and headache), reduced hepatotoxicity, reduced abuse potential, reduced $C_{max}$, a reduced level of active material even when chewed, reduced patient variability, and less variability between fed and fasted subjects.

By controlling the nature of the formulation, it is possible to control dissolution in vitro, and thus match or exceed the US National Formulary (NF) drug release profile for methylphenidate hydrochloride. Further, when administered to a healthy subject, a serum level of dtmp can be attained that is at least 50% of $C_{max}$, over a period of at least 8 hours, e.g. 8–16, 8–12 or 8–10 hours. Thus, for example, a shorter release period may be preferred or a different period before the serum level drops below a different proportion of $C_{max}$.

The serum level may be also controlled so that it remains high during the day, after taking a dosage in the morning, and is reduced in the evening, before it can have any undesirable effect on sleeping patterns.

A formulation of the invention may be a unit dosage such as a tablet, capsule or suspension. A sustained-release formulation may be in matrix, coating, reservoir, osmotic, ion-exchange or density exchange form. It may comprise a soluble polymer coating which is dissolved or eroded, after administration. Alternatively, there may be an insoluble coating, e.g. of a polymer, through which the active ingredient permeates, as from a reservoir, diffuses, e.g. through a porous matrix, or undergoes osmotic exchange. A further option for a sustained-release formulation involves density exchange, e.g. in the case where the formulation alters on administration, e.g. from microparticles to a gel, so that the active ingredient diffuses or permeates out. Ion-based resins may also be used, the active component being released by ionic exchange, and wherein the rate of release can be controlled by using cationic or anionic forms of the drug.

It is preferred to use a formulation in this invention that is resistant to chewing, e.g. micronised particles that are individually coated and which do not immediately release the active component on chewing, or possibly even actively discourage chewing by their consistency. Formulations of the invention that provide improved release characteristics may also be appropriate for the administration of racemic methylphenidate. Further, many effects, benefits etc. described herein apply to formulations providing immediate release. The various effects etc may be due to the use of dtmp and/or the absence of ltmp.

The other drug may be administered in admixture with the methylphenidate. Alternatively, it may be administered in any other formulation, via any suitable route of administration. Conventional dosing parameters may be adopted, i.e. those which are known to or adapted to the practice of those skilled in the art. For example, the daily dosage of dtmp may be 5 to 60 mg, but will be chosen according to the age, weight and health of the subject, and other factors that are routinely considered by the man skilled in the art.

The dtmp may be administered for its primary utility, i.e. treating hyperactive children, as a stimulant in cancer patients treated with narcotic analgesics, or for treating depression (e.g. in AIDS patients), compulsive shopping disorder, narcolepsy of hypersomnia. These subjects typically suffer other complaints requiring medication. The present invention is particularly adapted to the use of such other drugs, e.g. agents that are adapted to treat CNS disorders (e.g. depression); such agents may be tricyclic antidepressants or SSRIs. Thus, the other drug may be one that has the same mode of action, or which has a similar CNS activity. Alternatively or in addition, the other drug that is used in the invention may be any that undergoes the same metabolic degradation as ltmp, e.g. via the $P_{450}$ cytochromes, that interferes with ltmp metabolism, or that has its metabolism interfered with by ltmp.

There are many drugs that may interact with methylphenidate. Examples include anti-depressants.

Particularly drugs of interest are those whose metabolism is known to occur via the cytochrome $P_{450}$ pathways. For example, clomipramine, desipramine, indoramin, imipramine, phenformin and tropisetron undergo aromatic hydroxylation; amiflamine undergoes N-demethylation; amitriptyline and nortriptyline undergo benzylic hydroxylation; codeine, dextromethorphan, dihydrocodeine, hydrocodone, norcodeine and oxycodone undergo O-demethylation; ethylmorphine undergoes O-deethylation; flecainide and methoxyamphetamine undergo O-dealkylation; methoxyphenamine undergoes aromatic hydroxylation and N-demethylation; mexiletine and ondansetron undergo hydroxylation; perhexiline undergoes aliphatic hydroxylation; and thioridazine undergoes side-chain sulfoxidation. These are merely examples of drugs that use the given pathways. Other specific drugs of interest are cinnarizine, haloperidol, maprotiline, paroxetine and perphenazine.

Drugs of particular interest that have been seen to interact with methylphenidate include tricyclic anti-depressants (TCAs) such as amitriptyline, amoxapine, clomipramine, desipramine, doxepin, imipramine, maprotiline, nortriptyline, protriptyline or trimipramine; monoamine oxidase inhibitors such as phenelzine, selegeline or tranylcypromine; selective serotonin reuptake inhibitors (SSRIs) such as fluoxetine, paroxetine or sertraline; antipsychotics such as haloperidol; anticonvulsants/antiepileptics such as phenytoin, primidone and diphenylhydantoin; anticoagulants such as warfarin; and other drugs for which interactions have been reported such as isocarboxazid, metaraminol, phenylbutazone, phenylephrine, dopamide, norepinephrine, epinephrine, furazalidone, physostigmine and lithium.

It is often the case that a patient, typically a child, diagnosed as having attention-deficit hyperactivity disorder (ADHD; this term is used herein to include also attention-deficit disorder), has concomitant CNS disorders (whether or not diagnosed) which may require no immediate medication but which indicate the likelihood of a future need for, say, a SSRI or TCA. The use of dtmp is indicated, according to this invention, for such a patient.

Adverse effects (including cognitive and mood deterioration) were seen in children treated with a combination of imipramine and methylphenidate. Lithium significantly reduces the level of arousal-activation, euphoria-grandiosity, and the total score of manic-state ratings following methylphenidate challenge.

Further, of 20 patients treated with tricyclics combined with methylphenidate, 3 were withdrawn from the trial due to side-effects. These included dizziness, orthostatic blood pressure changes, dry mouth, increased anxiety and hypomania. Baclofen at 10 mg/kg produced a uniform block of both methylphenidate-enhanced activity and stereotypics in rats within 15 to 25 minutes when administered 10 minutes following methylphenidate. Physostigmine and methylphenidate are antagonised the effects of the other in the treatment of manic patients.

Metabolism of Methylphenidate by Cytochrome $P_{450}$

Experiments were carried out to investigate the effect of racemic methylphenidate, dtmp and ltmp on the hepatic cytochrome $P_{450}$ pathways. The experimental protocol utilised drugs known to be characteristically metabolised by a specific $P_{450}$ isotype, and measured the corresponding "enzyme activity" (see results Table, below) in human microsome preparations, by standard methods; see:

Tolbutamide: Knodell et al, J. Pharmacol. Exp. Thes. 241(3):1012–1019 (1987);

Mephenytoin: Yasumori et al, J. Pharmacol. Exp. Thes. 264(1):89–94 (1993);

Bufuralol: Kronbach et al, Anal. Biochem. 162:24–32 (1987); and

Lauric Acid: Okita et al, Methods in Enzymology 206:432–441 (1991).

The involvement of the particular $P_{450}$ isotype was confirmed using known standard inhibitor compounds (see results Table), using the indicated inhibitor concentrations. Methylphenidate, dtmp and ltmp were used at 100 μM.

| $P_{460}$ Isozyme | Enzyme Activity | Standard Inhibitor & Concentration (μM) | % Inhibition of Enzyme Activity | | | |
|---|---|---|---|---|---|---|
| | | | Standard Inhibitor | Racemic Methylphenidate | dtmp | ltmp |
| 2C9 | Tolbutamide hydroxylase | Sulphaphenazole (100) | >90 | 19 | 25 | 34 |
| 2C19 | Mephenytoin hydroxylase | Tranylcypronine (50) | 83 | 44 | 31 | 33 |
| 2D6 | Buturalol hydroxylase | Quinioline (10) | >90 | 65 | 64 | 41 |
| 28 | Lauric acid 11-hydroxylase | Disulfuran (10) | 47 | <15 | <20 | <20 |

The results shown that dtmp and ltmp have surprisingly similar profiles of inhibitory activity against the enzymes of the hepatic cytochrome $P_{450}$ pathway. Further, racemic methylphenidate appears more inhibitory of certain enzymes than either dtmp or ltmp. A reduction in the inhibition of the enzymes of the $P_{450}$ pathway may thus lead to a reduction in drug interaction.

What is claimed is:

1. A product comprising d-threo-methylphenidate and another drug, in which said another drug undergoes or interferes with $P_{450}$ metabolism, as a combined preparation for simultaneous, separate or sequential use in the treatment of conditions for which methylphenidate and said another drug are respectively adapted.

2. A product comprising d-threo-methylphenidate and another drug, in which the use of the d-threo-methylphenidate enantiomer reduces an undesirable side-effect compared to the use of the racemate with said another drug; as a combined preparation for simultaneous, separate or sequential use in the treatment of conditions for which methylphenidate and said another drug are respectively adapted.

3. The product according to claim 1, wherein said another drug is an anti-depressant.

4. The product according to claim 1, wherein the methylphenidate is for the treatment of a condition selected from depression, compulsive shopping disorder, narcolepsy, insomnia and attention-deficit hyperactivity disorder.

5. The product according to claim 1, wherein the product is formulated for administration to an adult patient.

6. The product according to claim 4, wherein the methylphenidate is for the treatment of attention-deficit hyperactivity disorder in a pre-pubertal child.

7. The product according to claim 1, for the treatment of a patient who is, or is susceptible to having a central nervous system disorder.

8. The product according to claim 1, wherein said another drug is selected from the group consisting of monoamine oxidase inhibitors, antipsychotics, anticonvulsants/antiepileptics, and anticoagulants.

9. The product according to claim 1, wherein said another drug is selected from the group consisting of isocarboxazid, metaraminol, phenylbutazone, phenylephrine, dopamide, norepinephrine, epinephrine, furazalidone, physostigmine and lithium.

10. The product according to claim 2, wherein said another drug is selected from the group consisting of monoamine oxidase inhibitors, antipsychotics, anticonvulsants/antiepileptics, and anticoagulants.

11. The product according to claim 2, wherein said another drug is selected from the group consisting of isocarboxazid, metaraminol, phenylbutazone, phenylephrine, dopamide, norepinephrine, epinephrine, furazalidone, physostigmine and lithium.

12. The product according to claim 2, wherein the undesirable side-effect is toxicity.

13. The product according to claim 3, wherein said antidepressant is selected from the group consisting of tricyclic antidepressants and selective serotonin reuptake inhibitors.

14. The product according to claim 7, for the treatment of a patient that has, or is susceptible to having anxiety, depression or epilepsy.

* * * * *